United States Patent

Matsumoto et al.

[11] Patent Number: 4,795,751
[45] Date of Patent: Jan. 3, 1989

[54] 5-SUBSTITUTED-6,8-DIFLUOROQUINO-LINES USEFUL AS ANTIBACTERIAL AGENTS

[75] Inventors: Jun-ichi Matsumoto, Ikoma; Teruyuki Miyamoto, Sakai; Hiroshi Egawa, Toyonaka; Shinichi Nakamura, Takatsuki, all of Japan

[73] Assignee: Dainippon Pharmaceutical Co., Ltd., Osaka, Japan

[21] Appl. No.: 928,297

[22] Filed: Oct. 28, 1986

[30] Foreign Application Priority Data

Oct. 29, 1985 [JP] Japan ................. 60-242257
Dec. 17, 1985 [JP] Japan ................. 60-285323
Feb. 17, 1986 [JP] Japan ................. 61-32627

[51] Int. Cl.$^4$ .............. A61K 31/47; A61K 31/53; C07D 215/56; C07D 401/04
[52] U.S. Cl. .................. 514/254; 514/218; 540/575; 544/363
[58] Field of Search .......... 544/363; 514/254

[56] References Cited

U.S. PATENT DOCUMENTS

| 3,753,993 | 8/1973 | Lesher et al. | 546/156 |
| 4,556,658 | 12/1985 | Grohe et al. | 544/363 |
| 4,559,341 | 12/1985 | Petersen et al. | 544/363 |
| 4,563,459 | 1/1986 | Grohe et al. | 544/363 |
| 4,636,506 | 1/1987 | Gilligan et al. | 546/156 |
| 4,668,680 | 5/1987 | Trehan et al. | 544/363 |

FOREIGN PATENT DOCUMENTS

| 178388 | 4/1986 | European Pat. Off. | 544/363 |
| 191185 | 8/1986 | European Pat. Off. | 514/254 |
| 216245 | 4/1987 | European Pat. Off. | 544/363 |
| 3306771 | 8/1984 | Fed. Rep. of Germany | 544/363 |
| 174367 | 10/1983 | Japan | 544/363 |
| 169475 | 9/1985 | Japan | 544/363 |
| 10574 | 1/1986 | Japan | 544/363 |

OTHER PUBLICATIONS

Mich et al, CA 105-97485j.

Primary Examiner—Donald G. Daus
Assistant Examiner—Cecilia Shen
Attorney, Agent, or Firm—Wenderoth, Lind & Ponack

[57] ABSTRACT

The present invention relates to a quinoline derivative of the formula

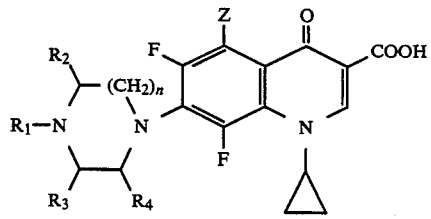

wherein
Z is an amino group or a halogen atom, $R_1$ is a hydrogen atom or a methyl or ethyl group, $R_2$ is a hydrogen atom or a methyl or fluoromethyl group, $R_3$ and $R_4$ are the same or different and each represents a hydrogen atom or a methyl group, and n is 1 or 2;

and esters thereof and salts thereof and processes for preparation thereof. These compounds show excellent antibacterial activity and are useful antibacterial agents.

11 Claims, No Drawings

5-SUBSTITUTED-6,8-DIFLUOROQUINOLINES USEFUL AS ANTIBACTERIAL AGENTS

This invention relates to novel quinoline compounds having very high antibacterial activity, and processes for preparing these compounds.

The compounds of this invention are quinoline derivatives represented by the following general formula

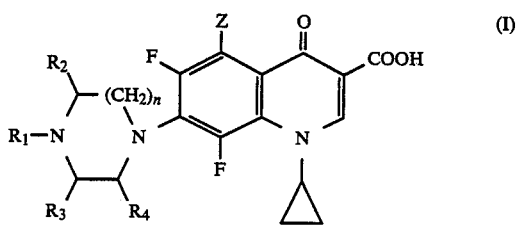

wherein
Z is an amino group or a halogen atom, $R_1$ is a hydrogen atom or a methyl or ethyl group, $R_2$ is a hydrogen atom or a methyl or fluoromethyl group, $R_3$ and $R_4$ are the same or different and each represents a hydrogen atom or a methyl group, and n is 1 or 2;
or esters thereof, or salts of said compounds or esters.

The salts of the compounds of formula (I) or their esters may be any salts formed from the compounds of formula (I) or their esters with pharmaceutically acceptable acids or bases. The salts of the compounds of the invention are the salts derived from inorganic acids such as hydrochloric acid or phosphoric acid; those from organic acids such as acetic acid, lactic acid, oxalic acid, succinic acid, methanesulfonic acid, maleic acid, malonic acid, or gluconic acid; those from acidic amino acids such as aspartic acid or glutamic acid; metal (e.g. sodium, potassium, calcium, magnesium, zinc or silver) salts; those from organic bases such as dimethylamine, triethylamine, dicyclohexylamine or benzylamine; and those from basic amino acids such as lysine or arginine.

The esters of the compounds of formula (I) include not only substituted or unsubstituted aliphatic esters, especially lower alkyl esters having 1 to 5 carbon atoms such as methyl or ethyl esters, but also esters that can be at least partially converted to the compounds (I) by chemical hydrolysis or by enzymatic hydrolysis in vivo, such as acetoxymethyl esters, pivaloyloxymethyl esters, ethoxycarbonyloxyethyl esters, choline esters, aminoethyl esters (e.g., dimethylaminoethyl or 1-piperidinylethyl esters), 5-indanyl esters, phthalidyl esters, and hydroxyalkyl esters (e.g., 2-hydroxyethyl or 2,3-dihydroxypropyl esters).

The compounds of formula (I), their esters, and salts of these compounds will therefore be generically referred to herein as the compounds of this invention.

The compounds of the invention may also exist as hydrates. Hence, these hydrates are also included in the compounds of this invention.

The compounds of the invention include those which have asymmetric carbon atoms on the piperazine ring at the 7-position and therefore exist in optically active forms. Hence, they include D isomers, L isomers and mixtures thereof.

Some of the compounds of this invention have two asymmetric carbon atoms on the piperazine ring at the 7-position and therefore can exist as stereoisomers having different configurations (cis or trans form). These stereoisomers and their mixtures are also included within the compounds of this invention.

The prior art on pharmaceutically effective compounds in this field will be discussed below.

Japanese Laid-Open Patent Publication No. 174367/1983 (an abstract of which is disclosed in Derwent World Patent Index, Accession No. 83-823272) discloses that compounds represented by the general formula (10)

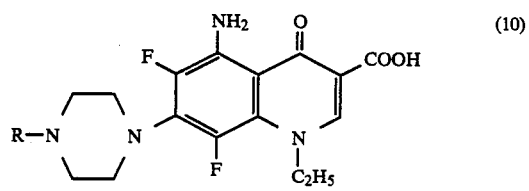

wherein
R represents a hydrogen atom or a lower alkyl group, have antibacterial activity. However, the compounds of the present invention have higher antibacterial activity than the above known compounds.

South African Laid-Open Patent Specification No. 8502369 discloses the following general formula (11)

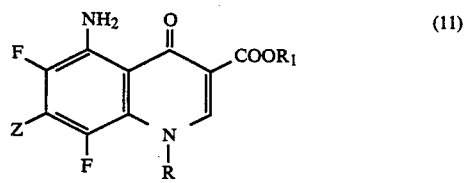

The specification does not disclose a cyclopropyl group as the group R in formula (11).

European Laid-Open Patent Specification No. 172651 discloses compounds represented by the following general formula (12)

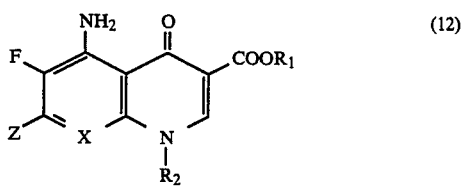

The specification does not disclose a piperazinyl group as the group Z in formula (12).

U.S. Pat. No. 4,556,658 discloses compounds represented by the following general formula (13)

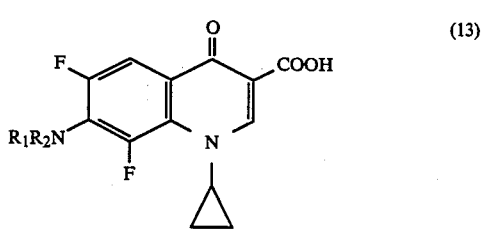

They, however, do not have an amino group at the 5-position of the quinoline ring as is clearly seen from formula (13).

It is an object of this invention to provide novel quinoline derivatives of formula (I) having high antibacterial activity against both Gram-positive bacteria and Gram-negative bacteria, esters thereof, and pharmaceutically acceptable salts of these, and processes for preparing these novel compounds.

Another object of this invention is to provide a pharmaceutical composition comprising an effective amount of a compound of formula (I), an ester thereof, or a pharmaceutically acceptable salt of any of these.

The invention further provides a method of treating bacterial infectious diseases of warm-blooded animals, which comprises administering the compounds or the pharmaceutical composition of this invention.

These and other objects of the invention will become apparent from the following description.

The compounds of this invention include the following compounds.

5-Amino-1-cyclopropyl-6,8-difluoro-7-(3-methyl-1-piperazinyl)-1,4-dihydro-4-oxoquinoline-3-carboxylic acid (compound 1) of the formula:

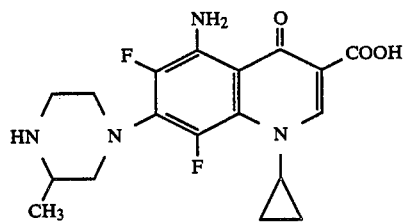

5-Amino-1-cyclopropyl-6,8-difluoro-7-(3,5-dimethyl-1-piperazinyl)-1,4-dihydro-4-oxoquinoline-3-carboxylic acid (compound 2) of the formula:

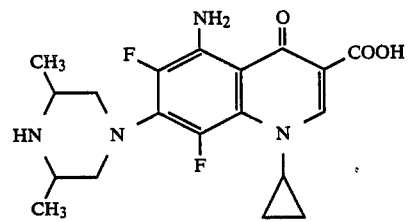

5-Amino-1-cyclopropyl-6,8-difluoro-7-(1-piperazinyl)-1,4-dihydro-4-oxoquinoline-3-carboxylic acid (compound 3) of the formula:

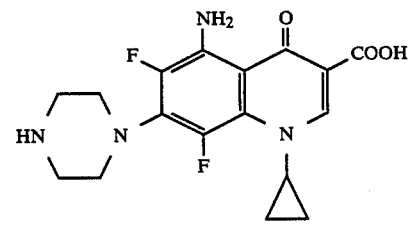

5-Amino-1-cyclopropyl-6,8-difluoro-7-(4-methyl-1-piperazinyl)-1,4-dihydro-4-oxoquinoline-3-carboxylic acid (compound 4) of the formula:

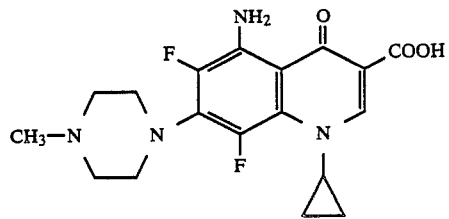

5-Amino-1-cyclopropyl-6,8-difluoro-7-(4-ethyl-1-piperazinyl)-1,4-dihydro-4-oxoquinoline-3-carboxylic acid (compound 5) of the formula:

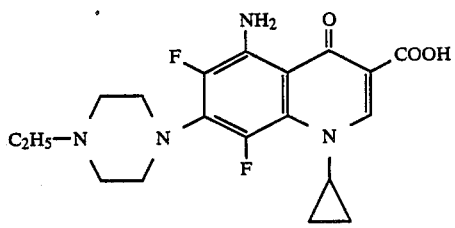

5-Amino-1-cyclopropyl-6,8-difluoro-7-(3-fluoromethyl-1-piperazinyl)-1,4-dihydro-4-oxoquinoline-3-carboxylic acid (compound 6) of the formula:

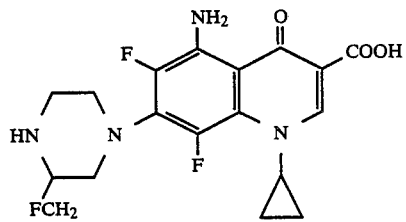

5-Amino-1-cyclopropyl-6,8-difluoro-7-(2-methyl-1-piperazinyl)-1,4-dihydro-4-oxoquinoline-3-carboxylic acid of the formula:

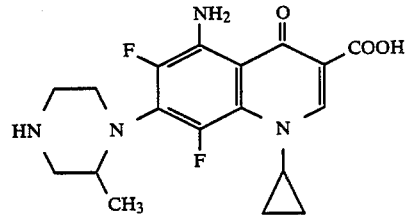

5-Amino-1-cyclopropyl-6,8-difluoro-7-(2,5-dimethyl-1-piperazinyl)-1,4-dihydro-4-oxoquinoline-3-carboxylic acid of the formula:

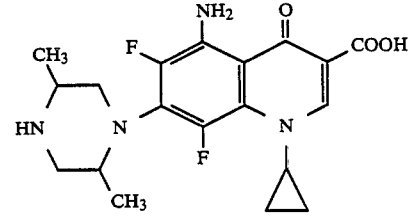

5-Amino-1-cyclopropyl-6,8-difluoro-7-(2,3-dimethyl-1-piperazinyl)-1,4-dihydro-4-oxoquinoline-3-carboxylic acid of the formula:

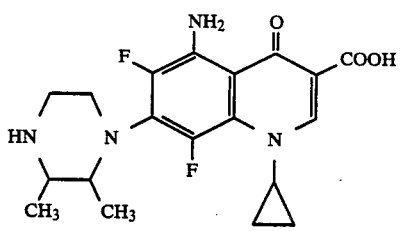

5-Amino-1-cyclopropyl-6,8-difluoro-7-(4-methyl-1-homopiperazinyl)-1,4-dihydro-4-oxoquinoline-3-carboxylic acid of the formula:

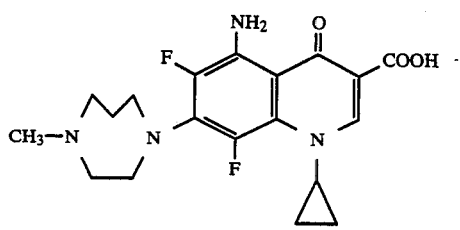

5-Amino-1-cyclopropyl-6,8-difluoro-7-(1-homopiperazinyl)-1,4-dihydro-4-oxoquinoline-3-carboxylic acid of the formula:

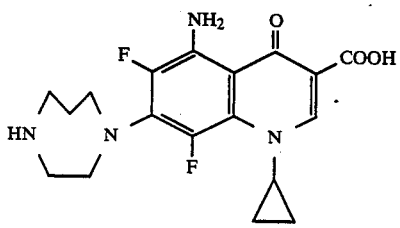

1-Cyclopropyl-5,6,8-trifluoro-7-(1-piperazinyl)-1,4-dihydro-4-oxoquinoline-3-carboxylic acid of the formula:

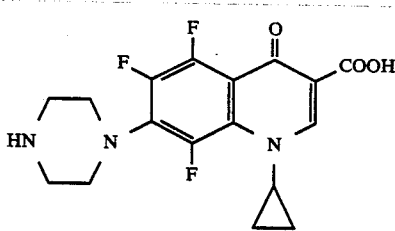

1-Cyclopropyl-5,6,8-trifluoro-7-(4-methyl-1-piperazinyl)-1,4-dihydro-4-oxoquinoline-3-carboxylic acid of the formula:

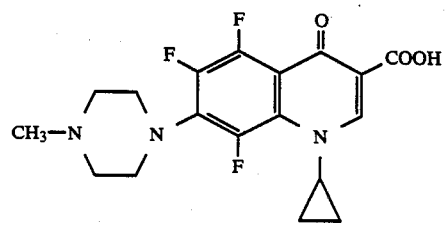

1-Cyclopropyl-5,6,8-trifluoro-7-(3-methyl-1-piperazinyl)-1,4-dihydro-4-oxoquinoline-3-carboxylic acid of the formula:

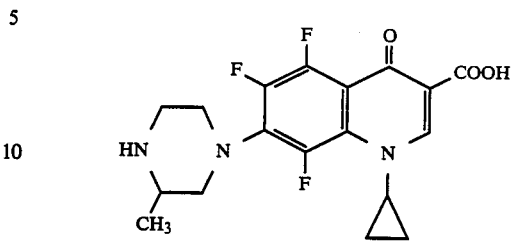

The compounds of this invention show excellent antibacterial activity and a broad antibacterial spectrum in in vitro tests. Furthermore, these compounds show an excellent infection-defending effect in vivo on topical or systemic infections caused by Gram-positive and Gram-negative bacteria.

The compounds of this invention also have excellent anti-mycoplasma activity.

The processes for preparing the compounds of this invention will be described below.

A. Substitution reaction by piperazine derivatives

The compounds of this invention can be produced by reacting a carboxylic acid or its ester (preferably a $C_1$-$C_5$ alkyl ester) represented by the following general formula

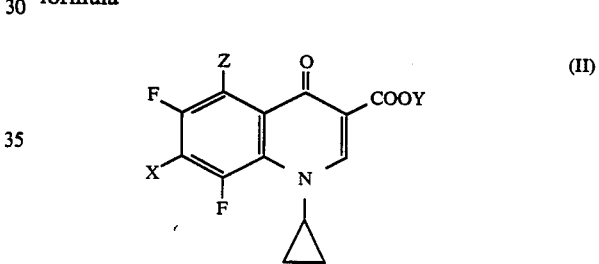

wherein
Z is an amino group or a halogen atom, X is a halogen atom, and Y is a hydrogen atom or an aliphatic group, with the proviso that when Z is a halogen atom, Y is a hydrogen atom, with a compound represented by the following general formula

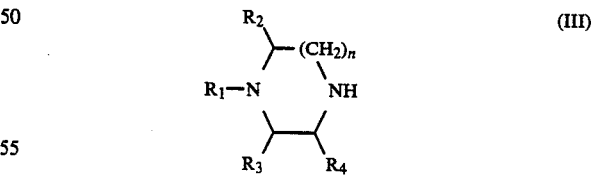

wherein
$R_1$, $R_2$, $R_3$, $R_4$ and n are as defined with respect to formula (I).

Examples of the halogen atom for X in formula (II) are fluorine, chlorine or bromine atoms.

This reaction can be carried out by stirring the starting compounds (II) and (III) at 10° to 180° C. for 10 minutes to 24 hours in an inert solvent. Examples of the inert solvent include alcohols such as ethanol, ethers such as dioxane, tetrahydrofuran and 1,2-dimethoxyethane, aromatic hydrocarbons such as benzene, toluene and xylene, acetonitrile, dimethylformamide, dimethyl sulfoxide, pyridine and water.

Generally, the above reaction is carried out in the presence of an acid acceptor using the starting compound of formula (III) in an amount equivalent or slightly excessive with regard to the starting compound (II). If desired, the starting compound (III) may be used in excess to make it serve concurrently as the acid acceptor. Examples of the acid acceptor are sodium hydrogen carbonate, sodium carbonate, potassium carbonate, triethylamine, pyridine, and picoline.

The starting compound (III) used in this reaction may, if possible, be used in a protected form, and after the reaction, its protective group is removed in a customary manner. The protective group may be any protective group which does not destroy the structure of the compounds of this invention formed by the reaction. Groups which are normally used as protective groups for the amino group in the field of chemistry of peptides, aminosugars, nucleic acids or beta-lactam compounds may be used in this invention.

The amino protective groups may be split off by solvolysis (including hydrolysis) or reduction depending upon the properties of the protective groups.

Specific examples of the protective groups capable of being eliminated by solvolysis include acyl groups such as formyl, acetyl and trifluoroacetyl; substituted or unsubstituted alkoxycarbonyl groups such as ethoxycarbonyl, t-butoxycarbonyl, benzyloxycarbonyl, p-methoxybenzyloxycarbonyl and beta-(p-toluenesulfonyl)-ethoxycarbonyl; a trityl group, a trimethylsilyl group, an o-nitrophenylsulfenyl group; a diphenylphosphinyl group; and a tetrahydropyranyl group.

This reaction is carried out in a solvent at 0° to 150° C. in the presence or absence of a catalyst such as an acid or base.

Examples of the acid are inorganic acids such as hydrochloric acid, hydrobromic acid, sulfuric acid and phosphoric acid; organic acids such as acetic acid, trifluoroacetic acid, formic acid, and toluenesulfonic acid; Lewis acids such as boron tribromide and aluminum chloride. Examples of the base are alkali metal hydroxides such as sodium hydroxide and barium hydroxide, alkali metal carbonates such as sodium carbonate and potassium carbonate; alkali metal alkoxides such as sodium methoxide and sodium ethoxide; and sodium acetate. Usually, water is used as the solvent. Depending upon the property of the compound, another solvent such as ethanol, dioxane, ethylene glycol dimethyl ether, benzene or acetic acid, or a mixed solvent of such a solvent with water may be used.

Examples of protective groups that may be eliminated by reduction include arylsulfonyl groups such as p-toluenesulfonyl; a methyl group substituted by phenyl or benzyloxy, such as benzyl, trityl or benzyloxymethyl; arylmethoxycarbonyl groups such as benzyloxycarbonyl and p-methoxybenzyloxycarbonyl; and halogenoethoxycarbonyl groups such as beta,beta,beta-trichloroethoxycarbonyl and beta-iodoethoxycarbonyl groups.

This reaction uses different reaction conditions depending upon the property of the protective group to be eliminated. For example, it is carried out by treating the compound with a hydrogen stream in an inert solvent at 10° to 60° C. in the presence of a catalyst such as platinum, palladium or Raney nickel; or treating it with metallic sodium in liquid ammonia usually at −50° to −20° C.; or by treating it with a metal such as zinc in acetic acid or in an alcohol such as methanol. Examples of the solvent in the catalytic reduction may include ethylene glycol dimethyl ether, dioxane, dimethylformamide, ethanol, ethyl acetate and acetic acid.

The starting compound (II) can be prepared by the methods described in Referential Examples 1 and 2 or methods substantially in accordance with them.

B. Amination reaction

The compounds of this invention can be prepared by reacting a carboxylic acid or its ester (preferably a $C_1$-$C_5$ alkyl ester) represented by the following general formula

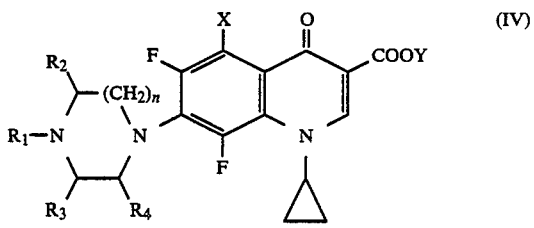

wherein
$R_1$, $R_2$, $R_3$, $R_4$, X, Y and n are as defined above, with ammonia.

This reaction can be carried out by contacting the starting compound (IV) with ammonia for 1 to 50 hours at a temperature of 50° to 150° C. in an inert solvent, for example an alcohol such as ethanol, pyridine, dimethylformamide or water, preferably in a sealed tube.

This reaction is carried out in the presence of an acid acceptor using ammonia in an amount equivalent to, or slightly in excess of, the starting compound (IV). Conveniently, ammonia is used in excess to make it serve also as the acid acceptor. A salt such as ammonium acetate may be caused to act instead of ammonia.

The starting compound (IV) used in this reaction may, if possible, be used in a form protected with such a protective group as described above in regard to reaction A, and after the reaction, the protective group is eliminated in a customary manner.

The starting compound (IV) is novel and can be prepared by the reaction A above.

C. Splitting off of the 5-amino protective group

The compound of this invention can be prepared by solvolyzing (also hydrolyzing) or reducing a compound represented by the following general formula

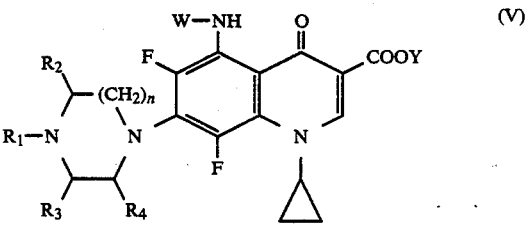

wherein
W is an amino-protective group, and $R_1$, $R_2$, $R_3$, $R_4$, Y and n are as defined hereinabove.

Examples of the amino-protective group W in formula (V) include acyl groups such as formyl, acetyl and trifluoroacetyl; alkoxycarbonyl groups such as ethoxycarbonyl and benzyloxycarbonyl; substituted methyl groups such as benzyl and benzhydryl; and a benzyloxy group.

This reaction is carried out in the same way as described hereinabove with regard to the elimination of the amino-protective group in reaction A.

The starting compound (V) used in this reaction may, if possible, be used in a form protected with such a protective group as is described with regard to reaction A, and after, or simultaneously with, the present reaction, the protective group is eliminated in a customary manner.

The starting compound (V) is a novel compound, and can be prepared by the methods described in Referential Examples 3 to 5 below, or methods substantially in accordance with them.

Where the compounds of this invention obtained by the above processes are esters, they can be converted to compounds of formula (I) by hydrolyzing the ester moiety in a customary manner. If required, the compounds of formula (I) may be esterified in a customary manner to form esters of the compounds of formula (I).

Pharmaceutically acceptable salts of the compounds of formula (I) or their esters may be produced by treating the compounds of formula (I) or esters thereof with acids, or by treating the compounds (I) with bases or metal salts. Acids suitable for salt formation include, for example, hydrochloric acid, phosphoric acid, acetic acid, lactic acid, oxalic acid, succinic acid, methanesulfonic acid, maleic acid, malonic acid, gluconic acid, aspartic acid and glutamic acid. Bases or metal salts suitable for salt formation include, for example, metal hydroxides such as sodium hydroxide and potassium hydroxide, metal carbonates such as sodium carbonate and potassium carbonate, zinc chloride, zinc sulfate, zinc nitrate and silver nitrate.

The compounds of this invention prepared as stated above are isolated and purified in a customary manner, and depending upon the isolating and purifying conditions, may be obtained in the form of a salt or a free acid. They may be converted into each other to produce the compounds of this invention in the desired forms.

The stereoisomers (cis and trans forms) of the compounds of this invention can be isolated by a conventional method such as fractional crystallization or chromatography. It is possible to produce compounds of this invention having a cis or trans configuration by the reaction A described above using the starting compounds (III) having a cis or trans configuration.

The optically active isomers of the compounds of this invention can be separated by known methods.

The compounds (I) thus obtained, their esters, and salts of these are all new compounds. In particular, the compounds (I) and their salts are valuable as antibacterial agents since they have very high antibacterial activity. The compounds (I) and their salts can be used not only as medicines for man and animals, but as fish medicines, agricultural chemicals and food perservatives. The esters of the compounds (I) are of course valuable as starting materials for synthesizing the compounds (I). When the esters can be easily transformed into the compounds (I) in vivo, they can exhibit an equivalent effect and are also useful as antibacterial agents.

Compounds (I) of this invention in which Z is a halogen atom are of course valuable as starting materials for compounds (I) in which Z is an amino group. They also have excellent antibacterial activity, low toxicity, good absorbability and good metabolism stability and are therefore useful as antibacterial agents administrable orally or by injection.

When the compounds of this invention are used as antibacterial agents for man, it is recommended that they be administered in a dose of 5 mg to 5 g per day once or several times daily, although the dose may be varied depending upon the age, body weight and symptom of a patient, the administration route, etc. The compounds may be administered orally or parenterally.

The compounds of this invention may be administered in their as-obtained powder form, but they are usually administered in the form of a pharmaceutical preparation together with pharmaceutically acceptable adjuvants. Specific examples of the pharmaceutical preparations are tablets, solutions, capsules, granules, fine granules, pellets, powders, syrups, injections, and ointments. These pharmaceutical preprations are prepared by methods known per se. Adjuvants for oral administration are those which are commonly used in the field of formulating pharmaceutical preparations and do not react with the compounds of the invention, such as starch, mannitol, crystalline cellulose, CMC Na, water, ethanol, etc. Adjuvants for injections are those commonly used in the field of injection such as water, isotonic sodium chloride solution, glucose solution and transfusion solution.

The above liquid preparations and ointments can also be used for local treatments in oto-rhino-laryngology or ophthalmology.

The following examples illustrate the production of the compounds of this invention more specifically.

REFERENTIAL EXAMPLE 1

1-Cyclopropyl-5,6,7,8-tetrafluoro-1,4-dihydro-4-oxoquinoline-3-carboxylic acid:

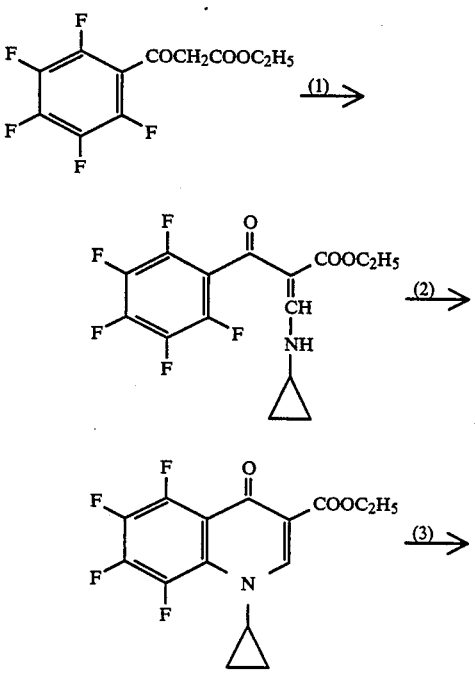

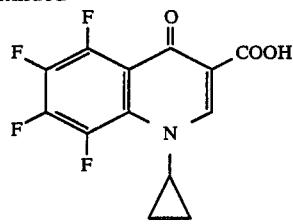

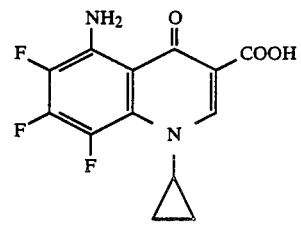

The numbers of the reaction steps described below correspond to the numbers in the above scheme.

(1) A mixture of the known compound, ethyl pentafluorobenzoylacetate J. Org. Chem., 35, 930 (1970)] (25 g), ethyl orthoformate (20 g), and acetic anhydride (23 g) was refluxed for 2 hours. The reaction mixture was evaporated to dryness under reduced pressure. The residue was dissolved in diethyl ether and allowed to react with cyclopropylamine (5.1 g) to give ethyl 2-pentafluorobenzoyl-3-cyclopropylaminoacrylate (28 g), m.p. 89° C.

(2) The above compound (28 g) was dissolved in dry tetrahydrofuran and allowed to react with 60% sodium hydride (3.85 g) at room temperature to give ethyl 1-cyclopropyl-5,6,7,8-tetrafluoro-1,4-dihydro-4-oxoquinoline-3-carboxylate (18.4 g), m.p. 170°–171° C.

(3) The above compound (10 g) was hydrolyzed by refluxing it in a mixture of glacial acetic acid (60 ml), water (500 ml) and concentrated sulfuric acid (7 ml) for 30 minutes to give 1-cyclopropyl-5,6,7,8-tetrafluoro-1,4-dihydro-4-oxoquinoline-3-carboxylic acid (8.7 g), m.p. 181°–182° C.

REFERENTIAL EXAMPLE 2

5-Amino-1-cyclopropyl-6,7,8-trifluoro-1,4-dihydro-4-oxoquinoline-3-carboxylic acid:

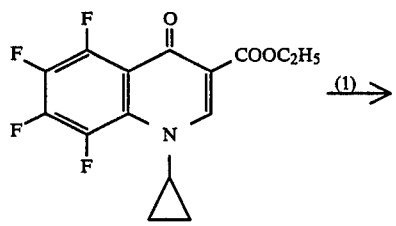

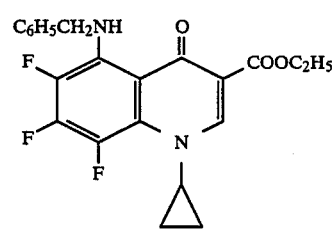

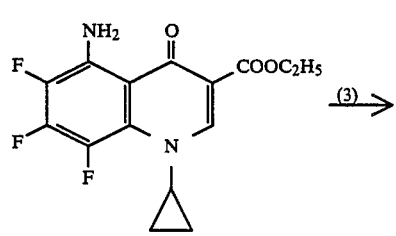

The numbers of the reaction steps described below correspond to the numbers in the above scheme.

(1) A mixture of ethyl 1-cyclopropyl-5,6,7,8-tetrafluoro-1,4-dihydro-4-oxoquinoline-3-carboxylate (28.2 g) prepared in Referential Example 1 (2), benzylamine (9.8 ml), anhydrous potassium carbonate (23.6 g), and acetonitrile (140 ml) was heated at 100°–110° C. for 1 hour to give ethyl 5-benzylamino-1-cyclopropyl-6,7,8-trifluoro-1,4-dihydro-4-oxoquinoline-3-carboxylate (21.4 g), which was recrystallized from ethanol, m.p. 134°–135° C.

(2) The above compound (20 g) was dissolved in acetic acid (100 ml) and ethanol (150 ml), and hydrogenolyzed in the presence of 5% palladium-carbon (0.5 g) to give ethyl 5-amino-1-cyclopropyl-6,7,8-trifluoro-1,4-dihydro-4-oxoquinoline-3-carboxylate (14.1 g), which was recrystallized from chloroform-ethanol, m.p. 236°–237° C.

(3) A mixture of the above compound (12.6 g), acetic acid (80 ml), water (50 ml), and concentrated sulfuric acid (9 ml) was heated at 100°–110° C. for 40 minutes to give 5-amino-1-cyclopropyl-6,7,8-trifluoro-1,4-dihydro-4-oxoquinoline-3-carboxylic acid (11.1 g), which was recrystallized from chloroform-ethanol, m.p. 294°–295° C.

EXAMPLE 1

5-Amino-1-cyclopropyl-6,8-difluoro-7-(3-methyl-1-piperazinyl)-1,4-dihydro-4-oxoquinoline-3-carboxylic acid and its hydrochloride:

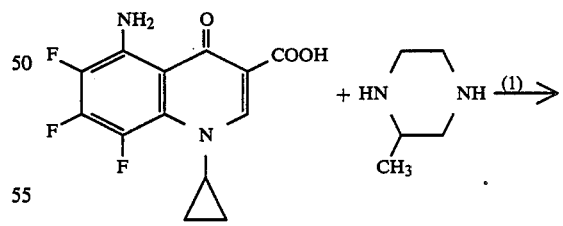

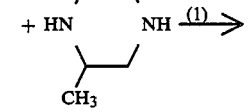

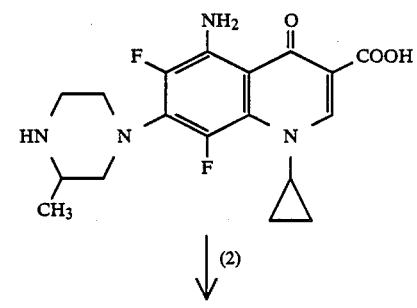

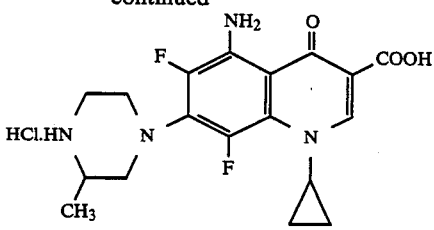

The numbers of the reaction steps described below correspond to the numbers in the above scheme.

(1) A mixture of 5-amino-1-cyclopropyl-6,7,8-trifluoro-1,4-dihydro-4-oxoquinoline-3-carboxylic acid (1.25 g), 2-methylpiperazine (2.0 g), and pyridine (13 ml) was heated at 105°–110° C. for 1 hour with stirring. The reaction mixture was evaporated to dryness under reduced pressure and water was added to the residue. The mixture was extracted with chloroform and the extract was dried. After evaporation of chloroform, ethanol was added to the residue. The resulting crystals were filtered and recrystallized from chloroform-ethanol to give 5-amino-1-cyclopropyl-6,8-difluoro-7-(3-methyl-1-piperazinyl)-1,4-dihydro-4-oxoquinoline-3-carboxylic acid (1.4 g), m.p. 251°–253° C.

(2) The above compound (700 mg) was dissolved in 20% hydrochloric acid (7 ml) and evaporated to dryness under reduced pressure. Ethanol was added to the residue and the resulting crystals were filtered and recrystallized from water-ethanol to give 5-amino-1-cyclopropyl-6,8-difluoro-7-(3-methyl-1-piperazinyl)-1,4-dihydro-4-oxoquinoline-3-carboxylic acid hydrochloride (425 mg), m.p. >300° C.

EXAMPLE 2

5-Amino-1-cyclopropyl-6,8-difluoro-7-(cis-3,5-dimethyl-1-piperazinyl)-1,4-dihydro-4-oxoquinoline-3-carboxylic acid:

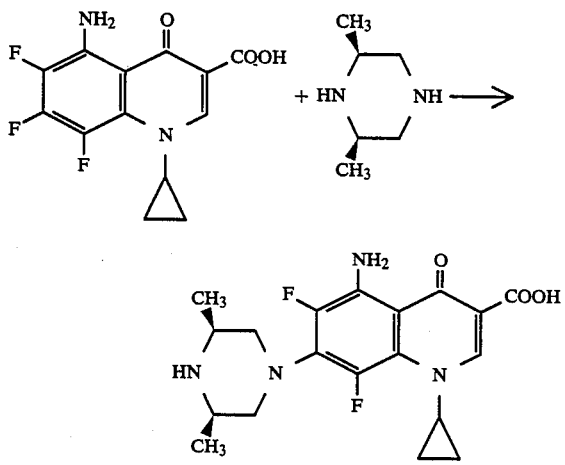

In the same manner as described in Example 1 (1), a mixture of 5-amino-1-cyclopropyl-6,7,8-trifluoro-1,4-dihydro-4-oxoquinoline-3-carboxylic acid, cis-2,6-dimethylpiperazine, and dimethylformamide was stirred at room temperature for 24 hours to give 5-amino-1-cyclopropyl-6,8-difluoro-7-(cis-3,5-dimethyl-1-piperazinyl)-1,4-dihydro-4-oxoquinoline-3-carboxylic acid, m.p. 258°–260° C.

EXAMPLE 3

5-Amino-1-cyclopropyl-6,8-difluoro-7-(1-piperazinyl)-1,4-dihydro-4-oxoquinoline-3-carboxylic acid and its hydrochloride:

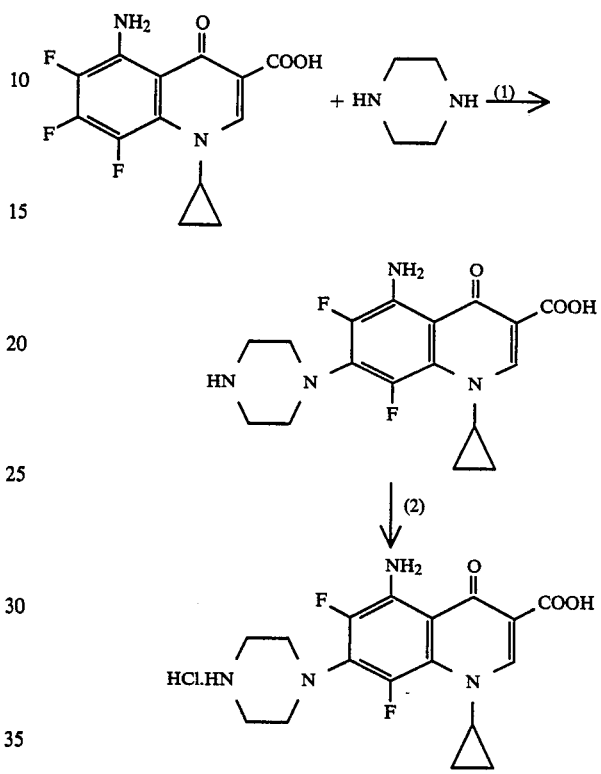

The numbers of the reaction steps described below correspond to the numbers in the above scheme.

(1) In the same manner as described in Example 1 (1), a mixture of 5-amino-1-cyclopropyl-6,7,8-trifluoro-1,4-dihydro-4-oxoquinoline-3-carboxylic acid, piperazine, and dioxane was refluxed for 5 hours to give 5-amino-1-cyclopropyl-6,8-difluoro-7-(1-piperazinyl)-1,4-dihydro-4-oxoquinoline-3-carboxylic acid, m.p. 263°–264° C.

(2) The above compound was treated in the same manner as described in Example 1 (2) to give 5-amino-1-cyclopropyl-6,8-difluoro-7-(1-piperazinyl)-1,4-dihydro-4-oxoquinoline-3-carboxylic acid hydrochloride, m.p. >300° C.

EXAMPLE 4

5-Amino-1-cyclopropyl-6,8-difluoro-7-(4-methyl-1-piperazinyl)-1,4-dihydro-4-oxoquinoline-3-carboxylic acid:

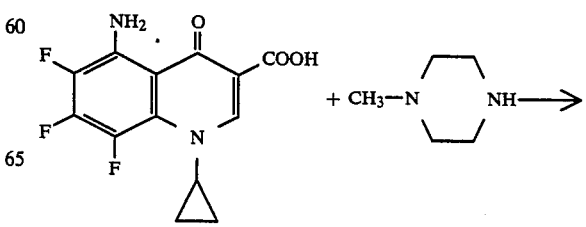

-continued

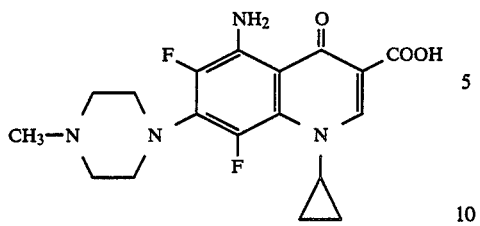

In the same manner as described in Example 1 (1), a mixture of 5-amino-1-cyclopropyl-6,7,8-trifluoro-1,4-dihydro-4-oxoquinoline-3-carboxylic acid, 1-methylpiperazine, and xylene was refluxed for 3 hours to give 5-amino-1-cyclopropyl-6,8-difluoro-7-(4-methyl-1-piperazinyl)-1,4-dihydro-4-oxoquinoline-3-carboxylic acid, m.p. 254°–255° C.

EXAMPLE 5

5-Amino-1-cyclopropyl-6,8-difluoro-7-(4-ethyl-1-piperazinyl)-1,4-dihydro-4-oxoquinoline-3-carboxylic acid:

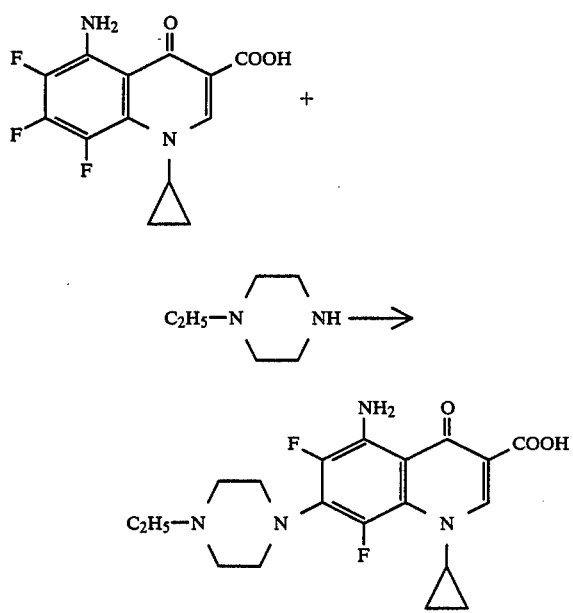

A mixture of 5-amino-1-cyclopropyl-6,7,8-trifluoro-1,4-dihydro-4-oxoquinoline-3-carboxylic acid, 1-ethylpiperazine, and acetonitrile was refluxed for 5 hours. After cooling, the resulting crystals were filtered, washed with water and recrystallized from ethanol to give 5-amino-1-cyclopropyl-6,8-difluoro-7-(4-ethyl-1-piperazinyl)-1,4-dihydro-4-oxoquinoline-3-carboxylic acid, m.p. 236°–237° C.

EXAMPLE 6

In the same manner as described in Example 5, the following compounds were obtained.

(a)  5-Amino-1-cyclopropyl-6,8-difluoro-7-(3-fluoromethyl-1-piperazinyl)-1,4-dihydro-4-oxoquinoline-3-carboxylic acid, m.p. 237°–238° C.

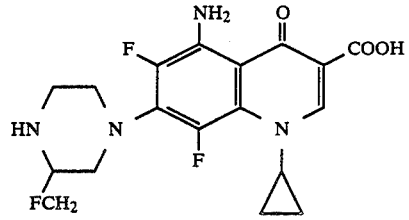

(b)  5-Amino-1-cyclopropyl-6,8-difluoro-7-(cis-2,3-dimethyl-1-piperazinyl)-1,4-dihydro-4-oxoquinoline-3-carboxylic acid trifluoroacetic acid salt, m.p. 250°–252° C. (decomp.)

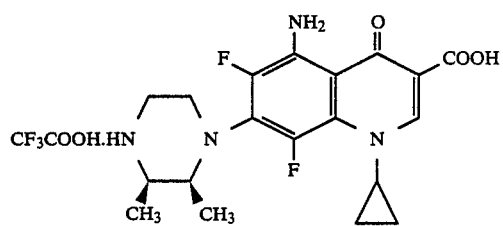

(c)  5-Amino-1-cyclopropyl-6,8-difluoro-7-(trans-2,5-dimethyl-1-piperazinyl)-1,4-dihydro-4-oxoquinoline-3-carboxylic acid, m.p. 235°–238° C.

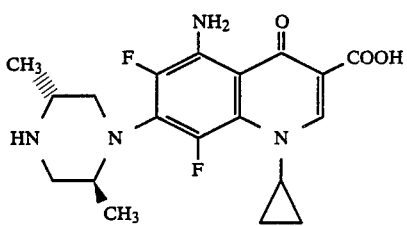

(d)  5-Amino-1-cyclopropyl-6,8-difluoro-7-(1-homopiperazinyl)-1,4-dihydro-4-oxoquinoline-3-carboxylic acid, m.p. 230°–233° C.

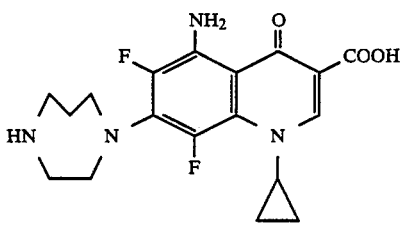

(e)  5-Amino-1-cyclopropyl-6,8-difluoro-7-(4-methyl-1-homopiperazinyl)-1,4-dihydro-4-oxoquinoline-3-carboxylic acid, m.p. 245°–248° C.

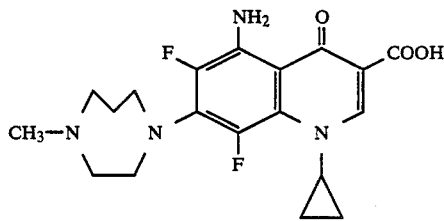

EXAMPLE 7

5-Amino-1-cyclopropyl-6,8-difluoro-7-(3-methyl-1-piperazinyl)-1,4-dihydro-4-oxoquinoline-3-carboxylic acid hydrochloride:

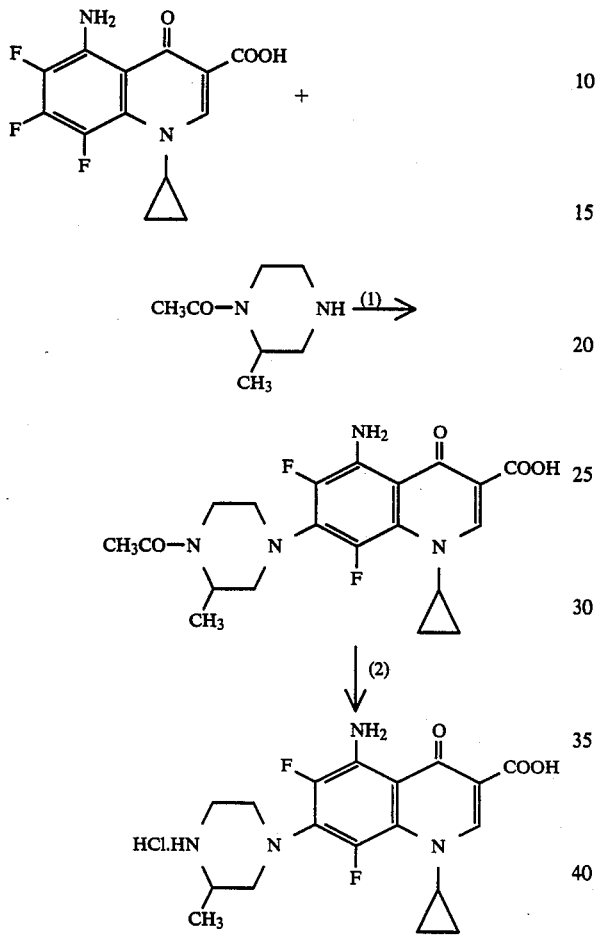

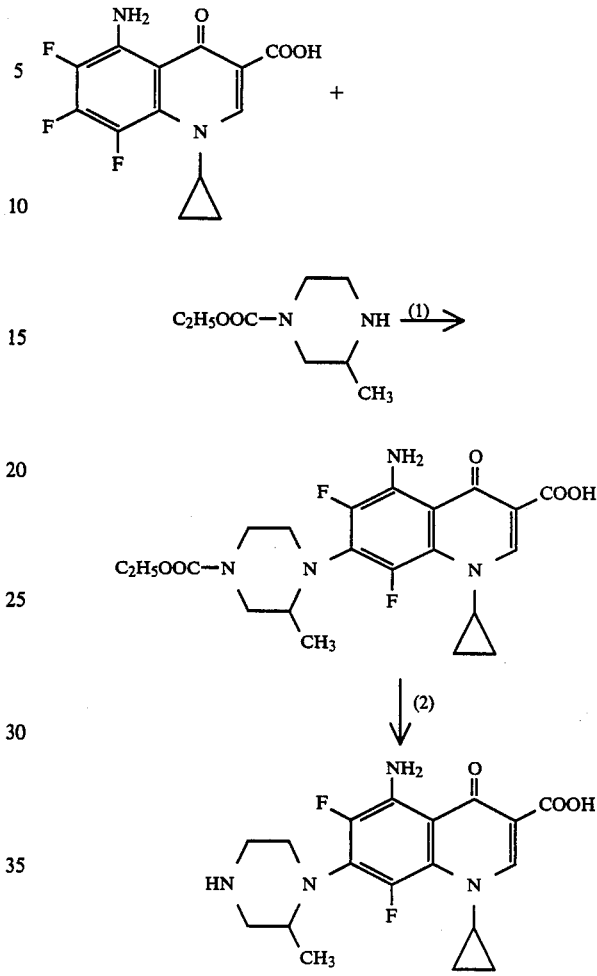

The numbers of the reaction steps described below correspond to the numbers in the above scheme.

(1) In the same manner as described in Example 1 (1) except using 1-acetyl-2-methylpiperazine in place of 2-methylpiperazine, 7-(4-acetyl-3-methyl-1-piperazinyl)-5-amino-1-cyclopropyl-6, 8-difluoro-1, 4-dihydro-4-oxoquinoline-3-carboxylic acid was obtained, m.p. 258°–260° C.

(2) A mixture of the above compound, 20% aqueous sodium hydroxide, and ethanol was refluxed for 12 hours. The reaction mixture was treated with activated carbon and adjusted to pH 1-2 with 10% hydrochloric acid. After cooling, the resulting crystals were filtered and recrystallized from water-ethanol to give 5-amino-1-cyclopropyl-6,8-difluoro-7-(3-methyl-1-piperazinyl)-1,4-dihydro-4-oxoquinoline-3-carboxylic acid hydrochloride, m.p. >300° C.

EXAMPLE 8

5-Amino-1-cyclopropyl-6,8-difluoro-7-(2-methyl-1-piperazinyl)-1,4-dihydro-4-oxoquinoline-3-carboxylic acid:

The numbers of the reaction steps described below correspond to the numbers in the above scheme.

(1) In the same manner as described in Example 1 (1), a mixture of 5-amino-1-cyclopropyl-6,7,8-trifluoro-1,4-dihydro-4-oxoquinoline-3-carboxylic acid, 1-ethoxycarbonyl-3-methyl-piperazine, and dimethyl sulfoxide was stirred at 150° C. for 2 hours to give 5-amino-1-cyclopropyl-6,8-difluoro-7-(4-ethoxycarbonyl-2-methyl-1-piperazinyl)-1,4-dihydro-4-oxoquinoline-3-carboxylic acid, m.p. 220°–225° C.

(2) The above compound was hydrolyzed in the same manner as described in Example 7 (2) and then the reaction mixture was neutralized. The resulting crystals were filtered and recrystallized from acetonitrile to give 5-amino-1-cyclopropyl-6,8-difluoro-7-(2-methyl-1-piperazinyl)-1,4-dihydro-4-oxoquinoline-3-carboxylic acid, m.p. 224°–226° C.

EXAMPLE 9

5-Amino-1-cyclopropyl-6,8-difluoro-7-(1-piperazinyl)-1,4-dihydro-4-oxoquinoline-3-carboxylic acid:

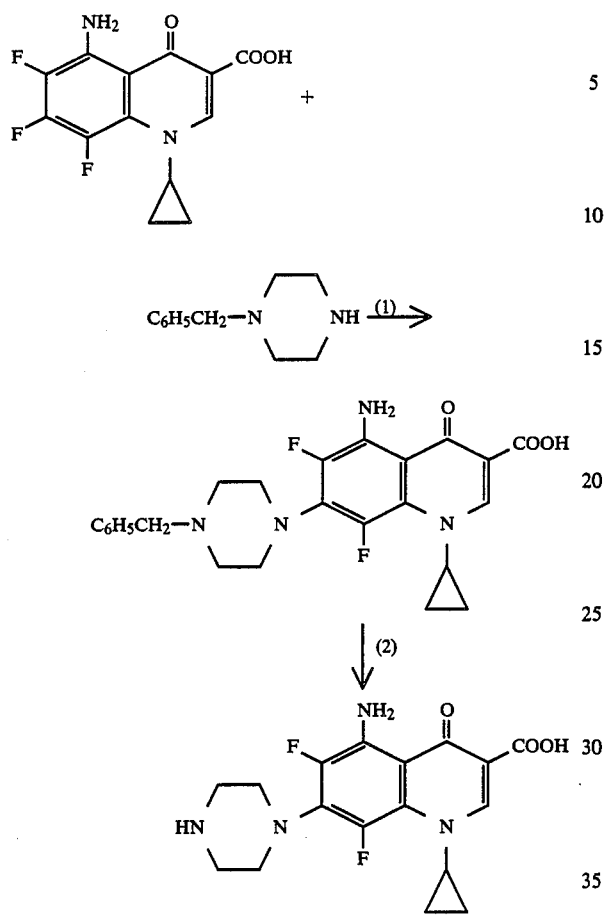

The numbers of the reaction steps described below correspond to the numbers in the above scheme.

(1) In the same manner as described in Example 1 (1) except using 1-benzylpiperazine in place of 2-methylpiperazine, 5-amino-1-cyclopropyl-6,8-difluoro-7-(4-benzyl-1-piperazinyl)-1,4-dihydro-4-oxoquinoline-3-carboxylic acid was obtained.

(2) The above compound was reduced catalytically in the presence of 5% palladium-carbon in acetic acide-thanol to give 5-amino-1-cyclopropyl-6,8-difluoro-7-(1-piperazinyl)-1,4-dihydro-4-oxoquinoline-3-carboxylic acid, m.p. 263°-264° C.

EXAMPLE 10

5-Amino-1-cyclopropyl-6,8-difluoro-7-(3-methyl-1-piperazinyl)-1,4-dihydro-4-oxoquinoline-3-carboxylic acid hydrochloride:

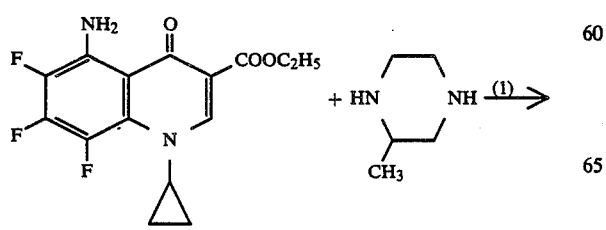

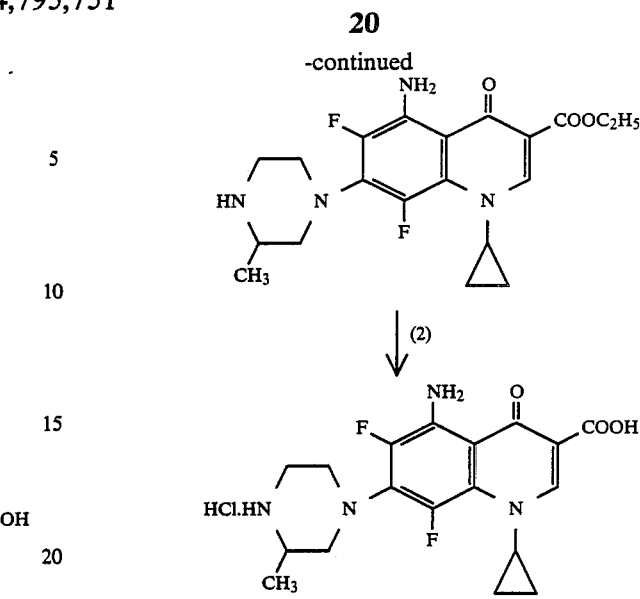

The numbers of the reaction steps described below correspond to the numbers in the above scheme.

(1) In the same manner as described in Example 1 (1) except using ethyl 5-amino-1-cyclopropyl-6,7,8-trifluoro-1,4-dihydro-4-oxoquinoline-3-carboxylate in place of -amino-1-cyclopropyl-6,7,8-trifluoro-1,4-dihydro-4-oxoquinoline-3-carboxylic acid, ethyl 5-amino-1-cyclopropyl-6,8-difluoro-7-(3-methyl-1-piperazinyl)-1,4-dihydro-4-oxoquinoline-3-carboxylate was obtained, m.p. 132°-134° C.

(2) The above compound was treated in the same manner as described in Example 7 (2) to give 5-amino-1-cyclopropyl-6,8-difluoro-7-(3-methyl-1-piperazinyl)-1,4-dihydro-4-oxoquinoline-3-carboxylic acid hydrochloride, m.p. >300° C.

EXAMPLE 11

1-Cyclopropyl-5,6,8-trifluoro-7-(3-methyl-1-piperazinyl)-1,4-dihydro-4-oxoquinoline-3-carboxylic acid:

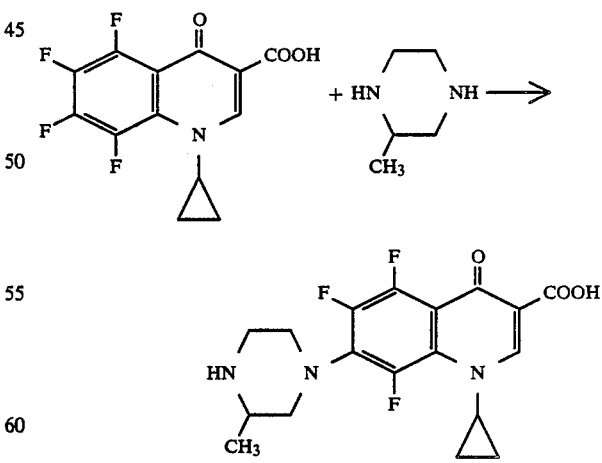

A mixture of 1-cyclopropyl-5,6,7,8-tetrafluoro-1,4-dihydro-4-oxoquinoline-3-carboxylic acid (910 mg), 2-methylpiperazine (320 mg), and pyridine (10 ml) was stirred at 80° C. for 1 hour. After evaporating the reaction mixture under reduced pressure, the residue was dissolved in dilute aqueous ammonia and treated with activated carbon. The filtrate was evaporated under reduced pressure and adjusted to pH 7-8. The resulting crystals were filtered, washed with water, and dried to give 1-cyclopropyl-5,6,8-trifluoro-7-(3-methyl-1-piperazinyl)-1,4-dihydro-4-oxoquinoline-3-carboxylic acid (810 mg), m.p. 235°-237° C.

EXAMPLE 12

In the same manner as described in Example 11, the following compounds were obtained.

(a) 1-Cyclopropyl-5,6,8-trifluoro-7-(1-piperazinyl)-1,4-dihydro-4-oxoquinoline-3-carboxylic acid, m.p. 208°-213° C.

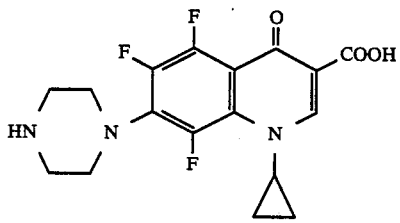

(b) 1-Cyclopropyl-5,6,8-trifluoro-7-(4-methyl-1-piperazinyl)-1,4-dihydro-4-oxoquinoline-3-carboxylic acid, m.p. 256° C.

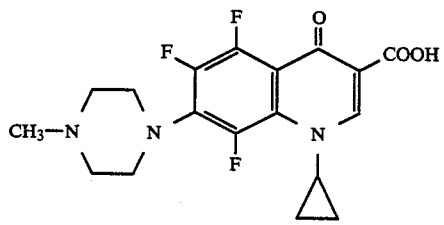

EXAMPLE 13

5-Amino-1-cyclopropyl-6,8-difluoro-7-(3-methyl-1-piperazinyl)-1,4-dihydro-4-oxoquinoline-3-carboxylic acid:

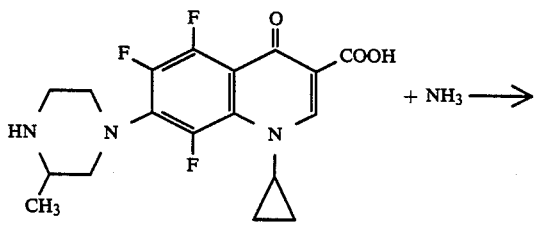

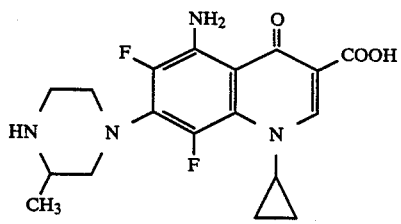

A mixture of 1-cyclopropyl-5,6,8-trifluoro-7-(3-methyl-1-piperazinyl)-1,4-dihydro-4-oxoquinoline-3-carboxylic acid (150 mg) and 28% aqueous ammonia (15 ml) was heated at 100° C. for 48 hours in a sealed tube. The reaction mixture was evaporated to dryness under reduced pressure and water was added to the residue. The mixture was extracted with chloroform. After drying, the extract was evaporated and the residue was recrystallized from chloroform-ethanol to give 5-amino-1-cyclopropyl-6,8-difluoro-7-(3-methyl-1-piperazinyl)-1,4-dihydro-4-oxoquinoline-3-carboxylic acid (93 mg), m.p. 251°-253° C.

EXAMPLE 14

5-Amino-1-cyclopropyl-6,8-difluoro-7-(1-piperazinyl)-1,4-dihydro-4-oxoquinoline-3-carboxylic acid:

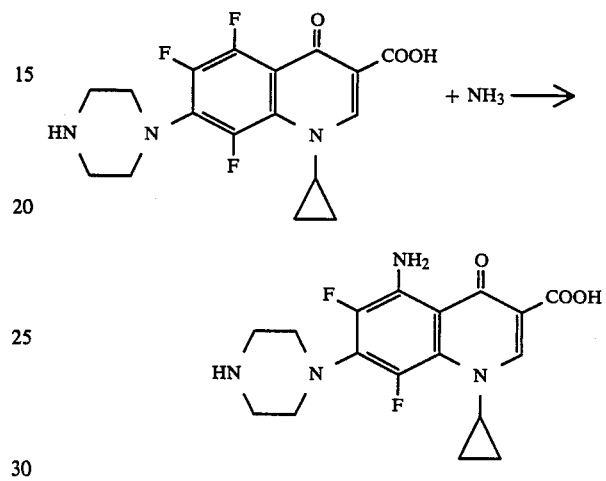

In the same manner as described in Example 13, 1-cyclopropyl-5,6,8-trifluoro-7-(1-piperazinyl)-1,4-dihydro-4-oxoquinoline-3-carboxylic acid was allowed to react with ammonia in ethanol in a sealed tube to give 5-amino-1-cyclopropyl-6,8-difluoro-7-(1-piperazinyl)-1,4-dihydro-4-oxoquinoline-3-carboxylic acid, m.p. 263°-264° C.

EXAMPLE 15

5-Amino-1-cyclopropyl-6,8-difluoro-7-(4-methyl-1-piperazinyl)-1,4-dihydro-4-oxoquinoline-3-carboxylic acid:

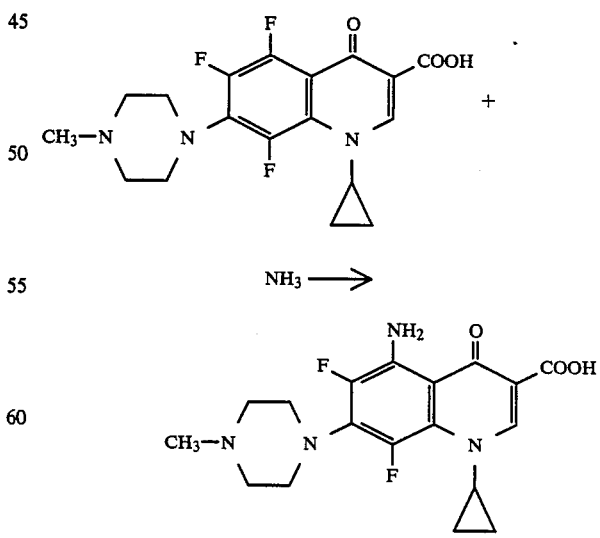

In the same manner as described in Example 13, 1-cyclopropyl-5,6,8-trifluoro-7-(4-methyl-1-piperazinyl)-1,4-dihydro-4-oxoquinoline-3-carboxylic acid was allowed to react with ammonia in dimethylformamide in a sealed tube to give 5-amino-1-cyclopropyl-6,8-difluoro-7-(4-methyl-1-piperazinyl)-1,4-dihydro-4-oxoquinoline-3-carboxylic acid, m.p. 254°–255° C.

REFERENTIAL EXAMPLE 3

5-Benzylamino-1-cyclopropyl-6,8-difluoro-7-(4-methyl-1-piperazinyl)-1,4-dihydro-4-oxoquinoline-3-carboxylic acid:

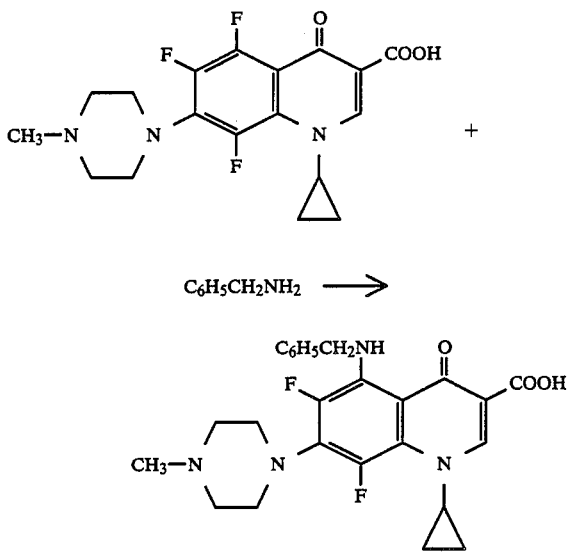

A mixture of 1-cyclopropyl-5,6,8-trifluoro-7-(4-methyl-1-piperazinyl)-1,4-dihydro-4-oxoquinoline-3-carboxylic acid (1.0 g), benzylamine (420 mg), and pyridine (5 ml) was heated at 100°–110° C. for 3 hours. The reaction mixture was evaporated to dryness under reduced pressure. After addition of water to the residue, the mixture was acidified with 10% aqueous acetic acid and extracted with chloroform. The extract was dried and evaporated. The resulting crystals were recrystallized from ethanol-ether to give 5-benzylamino-1-cyclopropyl-6,8-difluoro-7-(4-methyl-1-piperazinyl)-1,4-dihydro-4-oxoquinoline-3-carboxylic acid (730 mg), m.p. 132°–133° C.

EXAMPLE 16

5-Amino-1-cyclopropyl-6,8-difluoro-7-(4-methyl-1-piperazinyl)-1,4-dihydro-4-oxoquinoline-3-carboxylic acid:

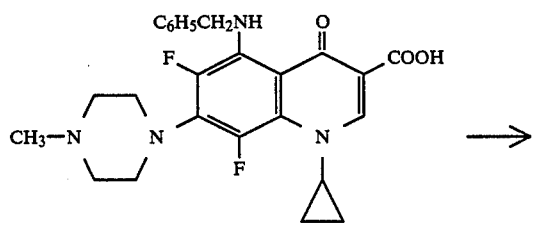

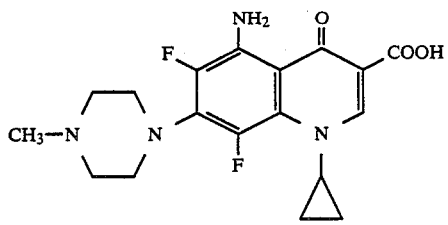

A mixture of 5-benzylamino-1-cyclopropyl-6,8-difluoro-7-(4-methyl-1-piperazinyl)-1,4-dihydro-4-oxoquinoline-3-carboxylic acid (700 mg), 5% palladium-carbon (0.2 g), acetic acid (10 ml), and ethanol (15 ml) was stirred at room temperature for 30 minutes under a hydrogen stream. The catalyst was filtered off and the filtrate was evaporated under reduced pressure. After addition of water to the residue, the mixture was adjusted to pH 8 with aqueous ammonia. The resulting crystals were filtered to give 5-amino-1-cyclopropyl-6,8-difluoro-7-(4-methyl-1-piperazinyl)-1,4-dihydro-4-oxoquinoline-3-carboxylic acid (510 mg), m.p. 254°–255° C.

REFERENTIAL EXAMPLE 4

Ethyl 1-cyclopropyl-5-ethoxycarbonylamino-6,8-difluoro-7-(3-methyl-1-piperazinyl)-1,4-dihydro-4-oxoquinoline-3-carboxylate:

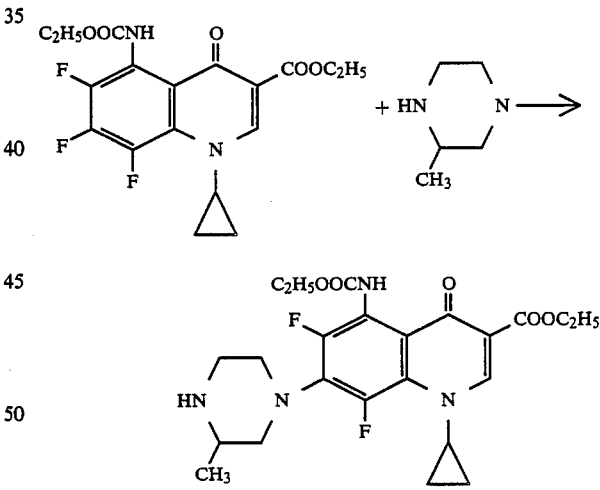

In the same manner as described in Example 1 (1), ethyl 1-cyclopropyl-5-ethoxycarbonylamino-6,7,8-trifluoro-1,4-dihydro-4-oxoquinoline-3-carboxylate (m.p. 189°–190° C.) was allowed to react with 2-methylpiperazine to give ethyl 1-cyclopropyl-5-ethoxycarbonylamino-6,8-difluoro-7-(3-methyl-1-piperazinyl)-1,4-dihydro-4-oxoquinoline-3-carboxylate.

EXAMPLE 17

5-Amino-1-cyclopropyl-6,8-difluoro-7-(3-methyl-1-piperazinyl)-1,4-dihydro-4-oxoquinoline-3-carboxylic acid hydrochloride:

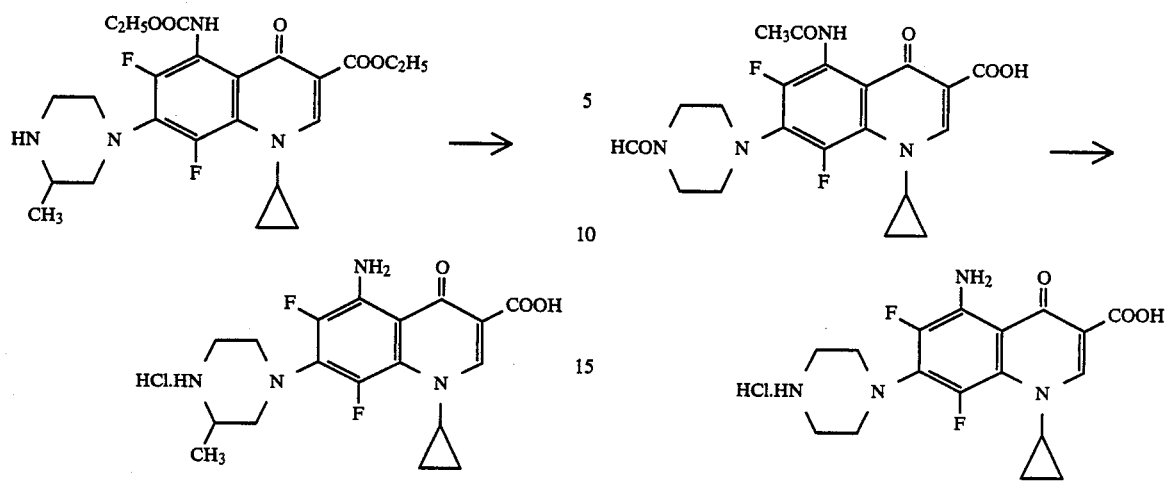

A mixture of ethyl 1-cyclopropyl-5-ethoxycarbonylamino-6,8-difluoro-7-(3-methyl-1-piperazinyl)-1,4-dihydro-4-oxoquinoline-3-carboxylate, 20% aqueous sodium hydroxide, and ethanol was refluxed for 12 hours. The reaction mixture was treated with activated carbon and adjusted at pH 1-2 with 10% hydrochloric acid. After cooling, the resulting crystals were collected by filtration and recrystallization from water-ethanol to give 5-amino-1-cyclopropyl-6,8-difluoro-7-(3-methyl-1-piperazinyl)-1,4-dihydro-4-oxoquinoline-3-carboxylic acid hydrochloride, m.p. >300° C.

REFERENTIAL EXAMPLE 5

5-Acetylamino-1-cyclopropyl-6,8-difluoro-7-(4-formyl-1-piperazinyl)-1,4-dihydro-4-oxoquinoline-3-carboxylic acid:

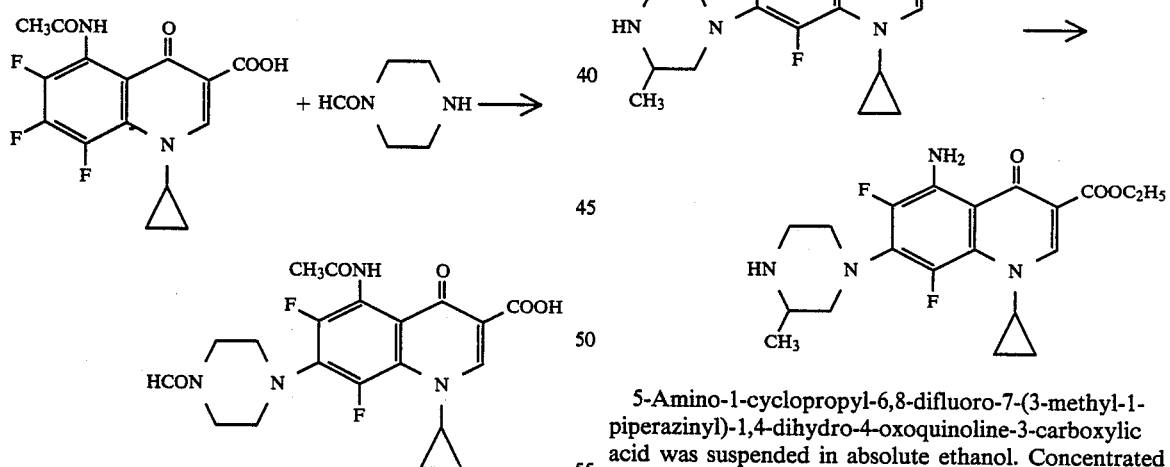

In the same manner as described in Example 1 (1), 5-acetylamino-1-cycloproply-6,7,8-trifluoro-1,4-dihydro-4- oxoquinoline-3-carboxylic acid (m.p. 247°-248° C.) was allowed to react with 1-formylpiperazine to give 5-acetylamino-1-cyclopropyl-6,8-difluoro-7-(4-formyl-1-piperazinyl)-1,4-dihydro-4-oxoquinoline-3-carboxylic acid.

EXAMPLE 18

5-Amino-1-cycloproply-6,8-difluroo-7-(1-piperazinyl)-1,4-dihydro-4-oxoquinoline-3-carboxylic acid hydrochloride:

5-Acetylamino-1-cyclopropyl-6,8-difluoro-7-(4-formyl-1-piperazinyl)-1,4-dihydro-4-oxoquinoline-3-carboxylic acid was treated in the same manner as described in Example 17 to give 5-amino-1-cyclopropyl-6,8-difluoro-7-(1-piperazinyl)-1,4-dihydro-4-oxoquinoline-3-carboxylic acid hydrochloride, m.p. >300° C.

EXAMPLE 19

Ethyl 5-amino-1-cyclopropyl-6,8-difluoro-7-(3-methyl-1-piperazinyl)-1,4-dihydro-4-oxoquinoline-3-carboxylate:

5-Amino-1-cyclopropyl-6,8-difluoro-7-(3-methyl-1-piperazinyl)-1,4-dihydro-4-oxoquinoline-3-carboxylic acid was suspended in absolute ethanol. Concentrated sulfuric acid was added to the suspension and the mixture was refluxed for 10 hours with stirring. After evaporation of ethanol, chloroform and a 20% aqueous sodium hydroxide solution were added to the residue, and the mixture was adjusted to pH 9. The organic layer was separated and chloroform was evaporated under reduced pressure. The resulting crystals were collected by filtration to give ethyl 5-amino-1-cyclopropyl-6,8-difluoro-7-(3-methyl-1-piperazinyl)-1,4-dihydro-4-oxoquinoline-3-carboxylate, m.p. 132°-134° C.

Examples 20 to 22 illustrate pharmaceutical compositions containing the compounds of the invention as active ingredients.

EXAMPLE 20

| Compound 1 or 3 | 250 g |
|---|---|
| Starch | 50 g |
| Talc | 15 g |

The above components were blended with ethanol and granulated and filled into 1,000 capsules in accordance with conventional methods.

EXAMPLE 21

| Compound 1 or 3 | 250 g |
|---|---|
| Starch | 54 g |
| Calcium carboxymethyl cellulose | 40 g |
| Microcrystalline cellulose | 50 g |
| Magnesium stearate | 6 g |

The above components were blended with ethanol and granulated and made into tablets in a manner known per se. Thus, 1,000 tablets each weighing 400 mg were formed.

EXAMPLE 22

| Compound 1 | 50 g |
|---|---|
| Lactic acid | 120 g |

The above components were dissolved in distilled water sufficient to make ten liters solution. The solution was adjusted to pH about 4 with an aqueous sodium hydroxide solution, and then filled in ampules (10 ml) to make an injectable solution.

The chemotherapeutic activities of the compounds of this invention are shown in Examples 23–26 hereinbelow. The compounds tested comprise:

Compound 1: 5-amino-1-cyclopropyl-6,8-difluoro-7-(3-methyl-1-piperazinyl)-1,4-dihydro-4-oxoquinoline-3-carboxylic acid, Compound 2: 5-amino-1-cyclopropyl-6,8-difluoro-7-(3,5-dimethyl-1-piperazinyl)-1,4-dihydro-4-oxoquinoline-3-carboxylic acid, Compound 3: 5-amino-1-cyclopropyl-6,8-difluoro-7-(1-piperazinyl)-1,4-dihydro-4-oxoquinoline-3-carboxylic acid, Compound 4: 5-amino-1-cyclopropyl-6,8-difluoro-7-(4-methyl-1-piperazinyl)-1,4-dihydro-4-oxoquinoline-3-carboxylic acid, Compound 5: 5-amino-1-cyclopropyl-6,8-difluoro-7-(4-ethyl-1-piperazinyl)-1,4-dihydro-4-oxoquinoline-3-carboxylic acid, Compound 6: 5-amino-1-cyclopropyl-6,8-difluoro-7-(3-fluoromethyl-1-piperazinyl)-1,4-dihydro-4-oxoquinoline-3-carboxylic acid, Compound A: 5-amino-1-ethyl-6,8-difluoro-7-(1-piperazinyl)-1,4-dihydro-4-oxoquinoline-3-carboxylic acid.

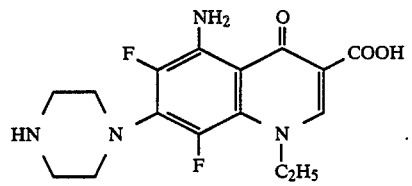

EXAMPLE 23

The antibacterial activity in vitro is shown in Table 1. The numbers in the table show minimum inhibitory concentrations (MIC) ($\mu$g/ml), calculated for free base. The minimum inhibitory concentration was determined by the twofold agar-dilution method, which was recommended by Japan Society of Chemotherapy (Chemotherapy, 29(1), 76(1981)), using Muller-Hinton agar. One loopful of an overnight culture of test organisms in Mueller-Hinton broth was inoculated onto 10-ml drug-containing agar layers in petri dishes. Bacterial inocula contained approximately $10^6$ colonyl-forming units. Bacterial growth was observed after 20-hour incubation at 37° C. The MIC was defined as the lowest drug concentration which prevented visible bacterial growth.

TABLE 1

| | In vitro antibacterial activity | | | | | | |
|---|---|---|---|---|---|---|---|
| | Compounds | | | | | | |
| Strains | 1 | 2 | 3 | 4 | 5 | 6 | A |
| Gram + | | | | | | | |
| S. aureus 209P JC-1 | 0.025 | 0.05 | 0.05 | 0.1 | 0.05 | 0.025 | 0.2 |
| S. aureus No. 50774 | 0.0125 | 0.025 | 0.05 | 0.05 | 0.025 | 0.0125 | 0.2 |
| S. aureus No. 80 | 0.0125 | 0.0125 | 0.05 | 0.025 | 0.025 | 0.0063 | 0.2 |
| S. epidermidis No. 8 | 0.025 | 0.025 | 0.05 | 0.05 | 0.05 | 0.025 | 0.39 |
| B. subtilis PCI 219 | 0.05 | 0.05 | 0.1 | 0.1 | 0.1 | 0.025 | 0.39 |
| Gram − | | | | | | | |
| Ac. calcoaceticus P-6901 | 0.0125 | 0.0125 | 0.05 | 0.025 | 0.0125 | 0.0063 | 0.2 |
| E. coli P-51213 | 0.025 | 0.05 | 0.1 | 0.1 | 0.05 | 0.05 | 0.39 |
| Al. faecalis P-7001 | 0.1 | 0.2 | 0.2 | 0.2 | 0.2 | 0.05 | 0.78 |
| P. aeruginosa No. 12 | 0.1 | 0.2 | 0.2 | 0.2 | 0.39 | 0.2 | 0.78 |
| M. bovis P-7101 | 0.2 | 0.39 | 0.39 | 0.39 | 0.39 | 0.1 | 3.13 |

EXAMPLE 24

In vivo efficacy against systemic infections in mice is shown in Table 2.

Compounds were each dissolved in deionized water. Each of the solutions was orally administered to mice infected with each of the test organisms under the conditions shown hereinbelow, and the median effective dose ($ED_{50}$) was calculated by probit analysis. The numerals in the table show $ED_{50}$ (mg/kg) value, calculated for free base.

Experimental conditions:

Mice: Male mice (ddY-S) weighing about 20 g

Infection:

*Staphylococcus aureus* 50774

Intravenous infection with $5 \times 10^8$ cells per mouse suspended in saline.

*Streptococcus pneumoniae* 1 Neufeld
  Intraperitoneal infection with $3\times 10^3$ cells per mouse suspended in brain heart infusion broth.
*Streptococcus pyogenes* A65
  Intraperitoneal infection with $3\times 10^7$ cells per mouse suspended in brain heart infusion broth.
*Pseudomonas aeruginosa* 12
  Intraperitoneal infection with about $5\times 10^3$ cells per mouse suspended in tryptosoy broth with 4% mucin.
Medication:
  Four times, immediately, 6, 24 and 30 hours after infection in case of Streptococcus pneumoniae 1 Neufeld. Twice, immediately and 6 hours after infection in case of other organisms.
Observation:
  For 14 days in case of *Staphylococcus aureus* 50774 and *Streptocuccus pneumoniae* 1 Neufeld. For 7 days in case of other organisms.

TABLE 2

In vivo efficacy against systemic infections in mice

| Strains | Compounds | |
|---|---|---|
| | 1 | A |
| S. aureus 50774 | 1.35 | — |
| S. pneumoniae I Neufeld | 10.9 | — |
| S. pyogenes A65 | 5.26 | >25 |
| P. aeruginosa 12 | 1.11 | 15.0 |

EXAMPLE 25

The anti-Mycoplasma activity of the compound 1 is shown in Table 3. The numbers in the table show minimum inhibitory concentrations (MIC) (μg/ml), calculated for free base. The minimum inhibitory concentration was determined by the twofold agar-dilution method using Chanock agar. Three μl of a culture of test organisms in Chanock broth was inoculated onto 10-ml drug-containing agar layers in petri dishes. Growth of Mycoplasma was observed after incubation at 37° C. under the conditions shown hereinbelow. The MIC was defined as the lowest drug concentration which prevented growth of Mycoplasma microscopically.
Incubation conditions:
  *Mycoplasma pneumoniae*
    For 7 days aerobically
  *Mycoplasma arginini* and *Acholeplasma laidlawii*
    For 2 days aerobically
  *Mycoplasma hyorhinis*
    For 3 days aerobically
  Other organisms
    For 2 days anaerobically

TABLE 3

Anti-Mycoplasma activity

| Strains | | Compound 1 |
|---|---|---|
| M. pneumoniae | Mac | 0.025 |
| M. orale | CH-19299 | 0.2 |
| M. hominis | PG-21 | 0.05 |
| M. fermentans | PG-18 | 0.0063 |
| M. salivarium | PG-21 | 0.2 |
| M. buccale | CH-20247 | 0.0125 |
| A. laidlawii | PG-8 | 0.1 |
| M. arginini | G-230 | 0.1 |
| M. hyorhinis | BST-7 | 0.2 |

EXAMPLE 26

The antibacterial activity of the compound 1 against *Campylobacter jejuni* is shown in Table 4. The numbers in the table show minimum inhibitory concentrations (MIC) (μg/ml), calculated for free base. The minimum inhibitory concentration was determined by the twofold agar-dilution method using blood-containing Mueller-Hinton agar. One loopful of a culture of test organisms in Mueller-Hinton broth was inoculated onto 10-ml drug-containing agar layer in petri dishes. Bacterial growth was observed after 48-hour incubation at 37° C. microaerobically. The MIC was defined as the lowest drug concentration which prevented visible bacterial growth.

TABLE 4

Antibacterial activity against *Campylobacter jejuni*

| Strains | Compound 1 |
|---|---|
| Campylobacter jejuni 10 | 0.0125 |
| Campylobacter jejuni 12 | 0.0125 |
| Campylobacter jejuni 20 | 0.0063 |
| Campylobacter jejuni 77 | 0.0125 |
| Campylobacter jejuni 170 | 0.0125 |
| Campylobacter jejuni A-11-3 | 0.05 |
| Campylobacter jejuni A-19-3 | 0.05 |
| Campylobacter jejuni A-24-2 | 0.05 |
| Campylobacter jejuni 19804 | 0.0125 |
| Campylobacter jejuni 19805 | 0.0125 |
| Campylobacter jejuni 19806 | 0.0125 |
| Campylobacter jejuni 19807 | 0.0125 |
| Campylobacter jejuni 10812 | 0.025 |

EXAMPLE 27

(Acute toxicity)

A solution containing each of compounds 1, 2 and 3 of this invention in various concentrations was orally given to male mice (ddY) at a dose of 0.1 ml per 10 g of body weight. The number of dead mice was counted after 7 days, and the value of median lethal dose ($LD_{50}$, mg/kg) was calculated in accordance with the Behrens-Kaerber method. The results are shown in Table 5.

TABLE 5

Acute oral toxicity in mice

| Compound | $LD_{50}$(mg/kg) |
|---|---|
| 1 | >2000 |
| 2 | >2000 |
| 3 | >2000 |

From the results shown in Table 5 it is seen that the compounds 1, 2, and 3 of this invention has low oral toxicity.

What is claimed is:

1. A member selected from the group consisting of (1) a compound of the formula

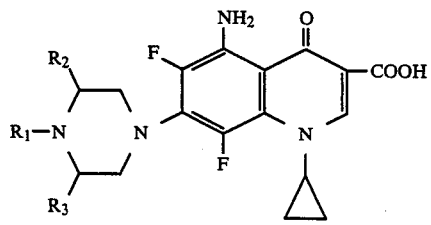

wherein

R₁ is a hydrogen atom or a methyl group, R₂ is a methyl or fluoromethyl group, and R₃ is a hydrogen atom or a methyl group, (2) a pharmaceutically acceptable ester thereof, and (3) a pharmaceutically acceptable salt of said compound (1) or said ester (2).

2. 5-Amino-1-cyclopropyl-6,8-difluoro-7-(3-methyl-1-piperazinyl)-1,4-dihydro-4-oxoquinoline-3-carboxylic acid or a pharmaceutically acceptable acid addition salt thereof.

3. 5-Amino-1-cyclopropyl-6,8-difluoro-7-(3,5-dimethyl-1-piperazinyl)-1,4-dihydro-4-oxoquinoline-3-carboxylic acid or a pharmaceutically acceptable acid addition salt thereof.

4. An antibacterial composition which comprises an antibacterially effective amount of a compound, ester or salt there of as defined in claim 1 and a pharmaceutically acceptable carrier therefor.

5. A method for the treatment of a bacterial infectious disease which comprises administering an antibacterially effective amount of a compound, ester or salt thereof as defined in claim 1 to a warm-blooded animal.

6. A member selected from the group consisting of (1) a compound of the formula

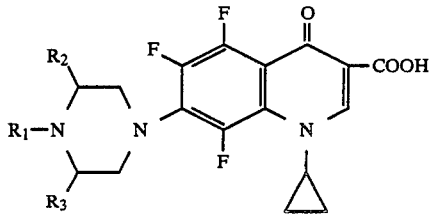

wherein

R₁ is a hydrogen atom or a methyl group, R₂ is a hydrogen atom or a methyl or fluoromethyl group, and R₃ is a hydrogen atom or a methyl group, (2) a pharmaceutically acceptale ester thereof, and (3) a pharmaceutically acceptable salt of said compound (1) or said ester (2).

7. 1-Cyclopropyl-5,6,8-trifluoro-7-(1-piperazinyl)-1,4-dihydro-4-oxoquinoline-3-carboxylic acid or a pharmaceutically acceptable acid addition salt thereof.

8. 1-Cyclopropyl-5,6,8-trifluoro-7-(4-methyl-1-piperazinyl)-1,4-dihydro-4-oxoquinoline-3-carboxylic acid or a pharmaceutically acceptable acid addition salt thereof.

9. 1-Cyclopropyl-5,6,8-trifluoro-7-(3-methyl-1-piperazinyl)-1,4-dihydro-4-oxoquinoline-3-carboxylic acid or a pharmaceutically acceptable acid addition salt thereof.

10. An antibacterial composition which comprises an antibacterially effective amount of a compound, ester or salt thereof as defined in claim 6 and a pharmaceutically acceptable carrier therefor.

11. A method for the treatment of a bacterial infectious disease which comprises administering an antibacterially effective amount of a compound, ester or salt thereof as defined in claim 6 to a warm-blooded animal.

* * * * *